United States Patent
Kim et al.

(10) Patent No.: US 11,214,558 B2
(45) Date of Patent: Jan. 4, 2022

(54) SYNTHESIS METHOD OF DHPV

(71) Applicants: SUNGKWANG MEDICAL FOUNDATION, Seoul (KR); CHA University Industry-Academic Cooperation Foundation, Pocheon-si (KR)

(72) Inventors: David Tae Aug Kim, Seoul (KR); A-Ram Kim, Goyang-si (KR); Young-Ger Suh, Seoul (KR); Jaehoon Sim, Seoul (KR)

(73) Assignees: SUNGKWANG MEDICAL FOUNDATION, Seoul (KR); CHA UNIVERSITY INDUSTRY-ACADEMIC COOPERATION FOUNDATION, Pocheon-si (KR)

( * ) Notice: Subject to any disclaimer, the term of this patent is extended or adjusted under 35 U.S.C. 154(b) by 0 days.

(21) Appl. No.: 16/967,797

(22) PCT Filed: Feb. 8, 2019

(86) PCT No.: PCT/KR2019/001584
§ 371 (c)(1),
(2) Date: Aug. 6, 2020

(87) PCT Pub. No.: WO2019/156510
PCT Pub. Date: Aug. 15, 2019

(65) Prior Publication Data
US 2021/0040056 A1 Feb. 11, 2021

(30) Foreign Application Priority Data
Feb. 8, 2018 (KR) .................. 10-2018-0015474

(51) Int. Cl.
C07D 307/33 (2006.01)
(52) U.S. Cl.
CPC ................. C07D 307/33 (2013.01)
(58) Field of Classification Search
CPC .................................................. C07D 307/33
See application file for complete search history.

(56) References Cited

FOREIGN PATENT DOCUMENTS

KR    10-2018-0078869    7/2018

OTHER PUBLICATIONS

KIPO, PCT Search Report & Written Opinion of PCT/KR2019/001584 dated May 13, 2019.
Masahiro Hamada et al., "Synthesis of Optically Pure Lactone Metabolites of Tea Catechins", Synthesis 2010(9): 1512-1520, DOI: 10.1055/s-0029-1218671.
Andreas Habel et al., "Efficient and flexible synthesis of chiral γ- and δ-lactonest", Organic & biomolecular chemistry, 6, 1601-1604, Mar. 10, 2008.
Jeremy P. E. Spencer et al., "Flavonoids and Related Compounds Bioavailability and Function", CRC Press, 2012, 1-452.
U. Kuchibhotla et al., "Selectivity and Reactivity in Some Oxidations With Pentavalent and Hexavalent Chromium Reagents: A Short Synthesis of Norbisabolide", Indian Journal of Chemistry, 1984, 23B, 1216-1218. DOI: 10.1002/chin.198521321.
Hiroyasu Watanabe, "The Chemical Structure of the Intermediate Metabolites of Catechin I-IV", Bull. Agric. Chem. Soc. Japan 1959, 23, 263. DOI: 10.1080/03758397.1959.10857572.
Joshua D. Lambert et al., "Synthesis and biological activity of the tea catechin metabolites, M4 and M6 and their methoxyderivatives", Bioorganic & Medicinal Chemistry Letters 15 (2005) 873-876, Jan. 18, 2005.
Masahiro Hamada et al., "Synthesis of Optically Pure Lactone Metabolites of Tea Catechins", Synthesis 2010, 1512-1520. DOI: 10.1055/s-0029-1218671.
Claudio Curti et al., "Catalytic, Enantioselective Vinylogous Mukaiyama Aldol Reaction of Furan-Based Dienoxy Silanes: A Chemodivergent Approach to γ-Valerolactone Flavan-3-ol Metabolites and δ-Lactone Analogues", Adv. Synth. Catal., 357, 4082-4092, Nov. 25, 2015. DOI: 10.1002/adsc.201500705.

*Primary Examiner* — Golam M Shameem
(74) *Attorney, Agent, or Firm* — Lex IP Meister, PLLC

(57) ABSTRACT

The present disclosure relates to a novel method for synthesizing DHPV, and more particularly, to a novel method for synthesizing DHPV (5-(3',4'-dihydroxyphenyl)-γ-valerolactone)) which is a major metabolite of cacao. This method has the advantage of not only facilitating a large-scale synthesis by a new synthesis method that can overcome existing defects, but also making it easy to select antioxidants and isomers exhibiting anti-aging bioactivities. Therefore, it is effective in enabling mass production of DHPV having high value as a functional material for cosmetics and pharmaceuticals in a simple and economical manner.

8 Claims, No Drawings

SYNTHESIS METHOD OF DHPV

CROSS-REFERENCE WITH RELATED APPLICATION(S)

This application claims the benefit of Korean Patent Application No. 10-2018-0015474 filed on Feb. 8, 2018 with the Korean Intellectual Property Office, the disclosure of which is incorporated herein by reference in its entirety.

TECHNICAL FIELD

The present disclosure relates to a novel method for synthesizing DHPV, and more particularly, to a novel method for synthesizing DHPV (5-(3',4'-dihydroxyphenyl)-γ-valerolactone)) which is a major metabolite of cacao.

BACKGROUND ART

DHPV is a major metabolite of cacao and is known to have an antioxidant effect and the like. However, cosmetics containing a low molecular weight compound derived from flavan-3-ol metabolite such as DHPV as a functional material have not yet been developed as products. However, due to its high membrane permeability, the low molecular weight compound has a high value as a functional cosmetic material for wrinkle improvement, such as the advantage of being able to reach the dermic layer more easily than macromolecule.

However, since DHPV is an in vivo metabolite of flavan-3-ol such as catechin, it was possible to extract and separate only a very small amount from natural resources. Thus, there was a problem that it was not easy to secure a sufficient amount of DHPV to proceed a subsequent study related to bioactivity. Therefore, famous domestic and foreign manufacturers are merely focusing on the commercialization of natural resource extracts themselves rather than the derivatives of naturally-occurring bioactive substances, and there was no room for securing new materials through medicinal and chemical approaches, such as large-scale synthesis of DHPV as a functional material, and research and development of derivatives. Therefore, research for total synthesis of DHPV has been conducted to solve the above problems, but it undergoes a long synthesis process of about seven to eight steps and is very complicated (Lambert, Bioorg. Med. Chem. Lett. 2005, 15, 873; Hamada, Synthesis 200, 1512), or it is difficult to handle and is harmful for the environment or human body (Curti, Adv. Synth. Catal. 2015, 357, 4082), or it is a synthesis using harsh reaction conditions (Watanabe, Bull. Agric. Chem. Soc. Japan 1959, 23, 263.). Therefore, there is a need to develop a new synthesis method capable of overcoming the above-mentioned problems.

DETAILED DESCRIPTION OF THE INVENTION

Technical Problem

Under these circumstances, the present inventors have conducted extensive studies to develop a commercial synthesis method of DHPV, and as a result, have found that, unlike a conventional synthesis method in which hydroxy hexanoate was synthesized and then gamma lactone was synthesized by transesterification which thus inevitably undergone a long synthesis step, the synthesis method of the present disclosure can be performed in a simple, practical and economical manner as compared with the conventional method, when the existing process step is reduced to one step by subjecting to oxidative cleavage from hexenol and then oxidation reaction, thereby completing the present disclosure.

Accordingly, one object of the present disclosure is to provide a novel method for preparing DHPV in a simple, practical and economical manner.

Technical Solution

In order to achieve the above object, according to one aspect of the present disclosure, there is provided a method for synthesizing DHPV of the following Chemical Formula 1 comprising the steps of:

a) reacting an aryl halide of the following Chemical Formula 2 with an epoxide compound of the following Chemical Formula 3 and undergoing epoxide ring-opening reaction to synthesize a hexenol compound of the following Chemical Formula 4;

b) oxidatively cleaving the hexenol compound of Chemical Formula 4 synthesized in step a) using a primary oxidizing agent, and then performing an oxidation reaction using a secondary oxidizing agent to obtain a gamma-lactone compound of the following Chemical Formula 5; and c) deprotecting the gamma-lactone compound of Chemical formula 5 obtained in step b).

[Chemical Formula 1]

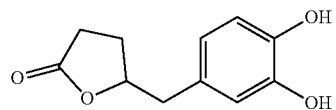

[Chemical Formula 2]

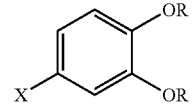

[Chemical Formula 3]

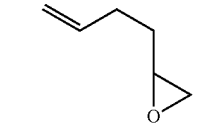

[Chemical Formula 4]

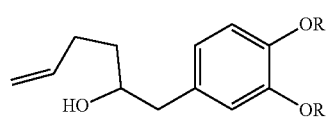

[Chemical Formula 5]

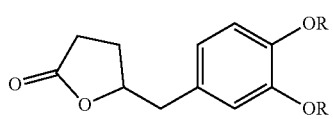

wherein,

X is Cl, Br, I, or trifluoromethanesulfonate (OTf; triflate), and

R is methyl (Me), methoxymethyl group (MOM), benzyl group (Bn), butyl diphenylsilyl group (TBDPS), butyldimethylsilyl group (TBS), dihydropyran group (THP), allyl group, acetyl group (Ac), or acetal group.

The preparation method of the present disclosure can be represented by the following Reaction Scheme 1.

[Reaction Scheme 1]

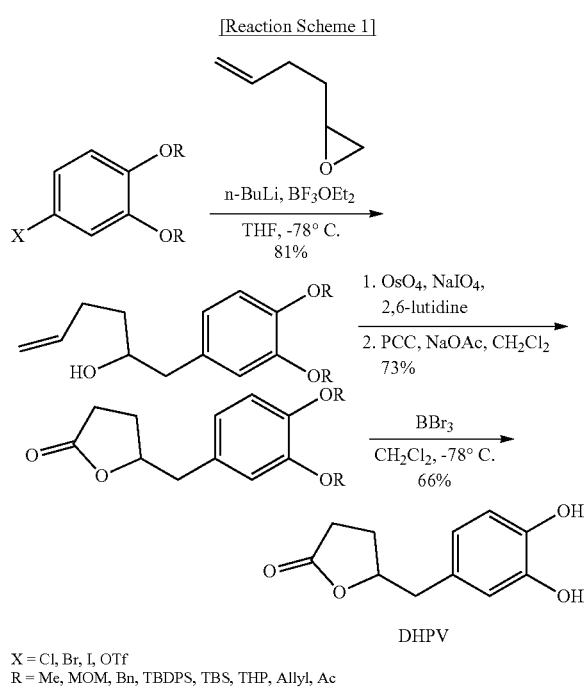

X = Cl, Br, I, OTf
R = Me, MOM, Bn, TBDPS, TBS, THP, Allyl, Ac

Thereinafter, each step of the preparation method will be described in detail.

The preparation method according to the present disclosure largely includes three steps as described above.

First, the first step (step a) is a step of reacting an epoxide with an aryl halide and undergoing an epoxide ring-opening reaction to synthesize a hexenol.

The aryl halide may be preferably a dihydroxy aryl halide, and may be in a form in which two types of hydroxy groups are protected by a protecting group. Specifically, examples of the aryl halide may include 4-bromo-1,2-dimethoxybenzene or 4-iodo-1,2-dihydroxybenzene, but the compound having an aryl halide structure may be appropriately selected and used without limitation. The protecting group may be methyl (Me), methoxymethyl group (MOM), benzyl group (Bn), butyldiphenylsilyl group (TBDPS), butyldimethylsilyl group (TBS), dihydropyran group (THP), allyl group (Allyl), acetyl group (Ac), acetal group, and it may be preferably a methyl group.

Further, the epoxide compound may be preferably 1,2-epoxy-5-hexene.

In a preferred embodiment, the aryl halide compound may be used in an amount of 1 to 10 equivalents based on 1 equivalent of the epoxide compound. Further, as the reaction solvent, tetrahydrofuran, diethyl ether, dimethoxyethane, dioxane, dimethylsulfoxide, dimethyl formamide or the like can be used, and it is preferably used in an amount of 0.01 mol to 10.0 mol. Furthermore, step a) is preferably performed at −80° C. to 25° C.

In the preparation method according to a specific embodiment of the present disclosure, 4-bromo-1,2-dimethoxybenzene was used as an aryl halide, 1,2-epoxy-5-hexene was used as a starting material, and n-BuLi, $BF_3OEt_2$ were used, and reacted in THF at −78° C. to give hexenol compound 1-(3,4-dimethoxyphenyl)hex-5-en-2-ol (yield: 81%).

The second step (step b) is a step of performing continuous oxidation reactions, that is, a primary oxidation reaction using a primary oxidizing agent, and a secondary oxidation reaction using a secondary oxidizing agent to synthesize a gamma-lactone. Preferably, the primary oxidizing agent used in the primary oxidation reaction may be $OsO_4$ (osmium tetroxide), $NaIO_4$ (sodium periodate), NMO (N-methylmorpholine oxide), $KHSO_5$ (potassium peroxymonosulfate), or a combination thereof, but is not limited thereto. The epoxide of hexenol having the epoxide group prepared in step b) is ring-opened using the primary oxidizing agent to synthesize lactol. Subsequently, the secondary oxidizing agent used in the secondary oxidation reaction may include pyridinium chlorochromate (PCC), pyridinium dichromate (PDC), potassium permanganate ($KMnO_4$), tetramethylpiperidinyloxy (TEMPO), ruthenium tetroxide ($RuO_4$), Dess-Martin periodinane (DMP), tetrapropylammonium perruthenate (TPAP), but is not limited thereto. The lactol compound may be secondarily oxidized to a gamma-lactone compound.

In a preferred embodiment, the primary oxidizing agent may be used in an amount of 0.01 to 50 equivalent weights based on 1 equivalent weight of the hexenol compound, and the secondary oxidizing agent may be used in an amount of 1 to 50 equivalent weights based on 1 equivalent weight of the lactol compound.

In the preparation method according to a specific embodiment of the present disclosure, the hexenol compound prepared in step a) was primarily oxidized using $OsO_4$ (osmium tetroxide), $NaIO_4$ and 2,6-lutidine and converted to a lactol compound, which is then secondarily oxidized using PCC, NaOAc and $CH_2Cl_2$ to obtain gamma-lactone compound (5-(3,4-dimethoxybenzyl)dihydrofuran-2(3H)one) (yield: 73%).

The last step, the third step (step c), is a step of deprotecting the protecting group protecting two hydroxy groups substituted on the phenyl group of the gamma-lactone compound prepared in step b). At this time, deprotection reaction is performed using boron tribromide ($BBr_3$), thiophenol (PHSH), lithium iodine (LiI), methyl magnesium iodine (MeMgI), lithium chloride (LiCl), trimethylsilyl iodine (TMSI), aluminum tribromide ($AlBr_3$), aluminum trichloride ($AlCl_3$), boron triiodide ($BI_3$), boron trifluoride ($BF_3$), boron trichloride ($BCl_3$) to finally obtain DHPV.

In a preferred embodiment, the boron tribromide may be used in an amount of 0.1 to 50 equivalent weights based on 1 equivalent weight of the lactone compound. Furthermore, step c) is preferably performed at −80° C. to 100° C.

In the preparation method according to a specific embodiment of the present disclosure, in order to remove the protecting group bound to the hydroxy group which is bound to the phenyl group of the gamma-lactone compound prepared in step b), the reaction was performed in dichloromethane ($CH_2Cl_2$) using $BBr_3$ at −78° C. to finally obtain DHPV (yield: 66%).

When DHPV is synthesized according to the preparation method of the present disclosure, it is possible to resolve the problem that, previously, there was no simple synthetic route for DHPV and thus it was difficult to mass-produce effectively in the process step, DHPV can be produced through a short and efficient synthesis route of 3 steps or less, and isomers of DHPV exhibiting antioxidant and anti-aging bioactivities can be selectively prepared. Therefore, not only it can be used as a raw material for anti-aging cosmetics but also it can facilitate mass production of DHPV which is also useful in the field of pharmaceutical chemistry.

Advantageous Effects

Although the antioxidant effect of DHPV has been significantly revealed through conventional studies, only a very small amount can be extracted and separated from natural resources, and so there has been no example applied to cosmetics and pharmaceuticals using it. However, the preparation method of the present disclosure as described above has the advantage of not only facilitating a large-scale synthesis by a new synthesis method that can overcome existing defects, but also making it easy to select antioxidants and isomers exhibiting anti-aging bioactivities. Therefore, it is effective in enabling mass production of DHPV having high value as functional cosmetic and pharmaceutical materials in a simple and economical manner.

DETAILED DESCRIPTION OF THE EMBODIMENTS

Hereinafter, the configuration of the present disclosure is described in more detail with reference to specific examples. However, it will be obvious to those skilled in the art these examples are provided for illustrative purposes only, and the scope of the present disclosure is not limited thereby.

Example 1. Synthesis of DHPV

DHPV was synthesized according to the following synthesis process.

The synthesis of DHPV was largely performed through three steps as shown in FIG. 1.

(a) Preparation of 1-(3,4-dimethoxyphenyl)hex-5-en-2-ol

4-Bromo-1,2-dimethoxybenzene (3.0 g, 13.8 mmol) was dissolved in anhydrous THF (15 ml) and cooled to −78° C., and then n-butyllithium (2.5 M, 6.1 ml, 15.2 mmol) was added drop by drop. After stirring for 40 minutes, BF3.OEt2 (1.9 ml, 15.2 mmol) and 2-(but-3-en-1-yl)oxirane (1.4 g, 13.8 mmol) were added. The mixture was stirred at room temperature for 24 hours, then treated with water, and the aqueous layer was extracted with ethyl acetate. The organic layer was washed once with saturated NaHCO$_3$ solution, dried over MgSO$_4$, filtered and concentrated under reduced pressure. The resulting residue was purified by silica gel chromatography to give a secondary alcohol. (yield: 81%, 2.6 g).

(b) Preparation of 5-(3,4-dimethoxybenzyl)dihydrofuran-2(3H)-one

The compound (1.0 g, 4.2 mmol) obtained in step (a) was dissolved in 1,4-dioxane (4 ml) and water (1 ml), and 2,6-lutidine (0.97 ml, 8.4 mmol) and O$_s$O$_4$ were added thereto. After cooling to 0° C., sodium periodate (3.6 g, 16.8 mmol) was added. The mixture was stirred at room temperature for 17 hours, then treated with water, and the aqueous layer was extracted with CH$_2$Cl$_2$. The organic layer was washed with brine, dried over MgSO$_4$, filtered and concentrated under reduced pressure to obtain a lactol compound. The obtained lactol compound was dissolved in CH$_2$Cl$_2$ (5 ml), cooled to 0° C., and then sodium acetate (688 mg, 8.4 mmol) and pyridinium chlorochromate (1.8 g, 8.4 mmol) were slowly added. The mixture was stirred at room temperature for 1 hour, and then immediately purified by silica gel chromatography to give a lactone compound. (yield: 73%, 724 mg).

(c) Preparation of 5-(3,4-dihydroxyphenyl)-γ-valerolactone

The lactone compound (500 mg, 2.1 mmol) obtained in step b) was dissolved in CH$_2$Cl$_2$ (2 ml), cooled to −78° C., and then borontribromide (0.81 ml, 8.4 mmol) was added. The mixture was stirred at room temperature for 10 hours, then treated with water, and the aqueous layer was extracted with CH$_2$Cl$_2$. The organic layer was washed with brine, dried over MgSO$_4$, filtered and concentrated under reduced pressure. The resulting residue was purified by silica gel chromatography to give a white solid valerolactone. (yield: 66%, 288 mg).

DHPV; $^1$H-NMR (CDCl$_3$, 800 MHz) δ 6.69 (s, 1H), 6.68 (t, J=2.8 Hz, 1H), 6.55 (dd, J=8.0, 2.9 Hz, 1H), 4.72 (td, J=10.1, 6.2 Hz, 1H), 2.87 (dd, J=14.1, 6.1 Hz, 1H), 2.78 (dd, J=14.1, 6.1 Hz, 1H), 2.47 (td, J=13.4, 9.3 Hz, 1H), 2.32 (dq, J=17.7, 4.8 Hz, 1H), 2.23 (m, 1H), 1.95 (m, 1H); $^{13}$C-NMR (CDCl$_3$, 200 MHz) δ 181.1, 147.1, 146.1, 129.8, 122.7, 118.5, 117.2, 84.1, 42.3, 30.3, 29.7; HR-MS (FAB+) calcd for C$_{11}$H$_{13}$O$_4$ (M+H$^+$) 209.0814; found 209.0820.

The invention claimed is:

1. A method for preparing DHPV of the following Chemical Formula 1 comprising the steps of:
   a) reacting an aryl halide of the following Chemical Formula 2 with an epoxide compound of the following Chemical Formula 3 and undergoing epoxide ring-opening reaction to synthesize a hexenol compound of the following Chemical Formula 4;
   b) oxidatively cleaving the hexenol compound of Chemical Formula 4 synthesized in step a) using a primary oxidizing agent, and then performing an oxidation reaction using a secondary oxidizing agent to obtain a gamma-lactone compound of the following Chemical Formula 5; and
   c) deprotecting the gamma-lactone compound of Chemical formula 5 obtained in step b) using BBr$_3$,

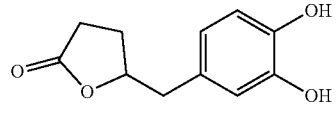

[Chemical Formula 1]

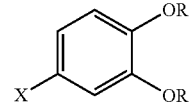

[Chemical Formula 2]

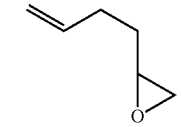

[Chemical Formula 3]

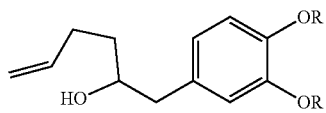

[Chemical Formula 4]

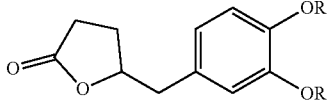

[Chemical Formula 5]

wherein,

X is Cl, Br, I, or trifluoromethanesulfonate (OTf; triflate), and

R is methyl (Me), methoxymethyl group (MOM), benzyl group (Bn), butyl diphenylsilyl group (TBDPS), butyldimethylsilyl group (TBS), dihydropyran group (THP), allyl group, acetyl group (Ac), or acetal group.

2. The preparation method of claim 1, wherein the aryl halide is 4-bromo-1,2-dimethoxybenzene, 3,4-dihydroxyphenyl iodide, or a combination thereof.

3. The preparation method of claim 1, wherein the epoxide compound is 1,2-epoxy-5-hexene.

4. The preparation method of claim 1, wherein the aryl halide compound is used in an amount of 1 to 10 equivalent weights based on 1 equivalent weight of the epoxide compound.

5. The preparation method of claim 1, wherein the primary oxidizing agent in step b is $O_5O_4$ (osmium tetroxide), $NaIO_4$ (sodium periodate), NMO (N-methylmorpholine oxide), $KHSO_5$ (potassium peroxymonosulfate), or a combination thereof.

6. The preparation method of claim 1, wherein the secondary oxidizing agent in step b is pyridinium chlorochromate (PCC), pyridinium dichromate (PDC), potassium permanganate ($KMnO_4$), tetramethylpiperidinyloxy (TEMPO), ruthenium tetroxide ($RuO_4$), Dess-Martin periodinane (DMP), or tetrapropylammonium perruthenate (TPAP).

7. The preparation method of claim 1, wherein in step b, the primary oxidizing agent is used in an amount of 0.01 to 50 equivalent weights based on 1 equivalent weight of a hexanol compound, and the secondary oxidizing agent is used in an amount of 1 to 50 equivalent weights based on 1 equivalent weight of a lactol compound.

8. The preparation method of claim 1, wherein in step c, the boron tribromide is used in an amount of 0.1 to 50 equivalents based on 1 equivalent of the lactone compound.

* * * * *